United States Patent
Langelier et al.

(10) Patent No.: US 6,524,821 B1
(45) Date of Patent: Feb. 25, 2003

(54) ANTI-APOPTOTIC COMPOSITIONS COMPRISING THE R1 SUBUNIT OF HERPES SIMPLEX VIRUS RIBONUCLEOTIDE REDUCTASE OR ITS N-TERMINAL PORTION; AND USES THEREOF

(75) Inventors: Yves Langelier, Montreal (CA); Bernard Massie, Montreal (CA)

(73) Assignee: Centre de Recherche du Centre Hospitalier de l'Université de Montréal, Montreal (CA)

( * ) Notice: Subject to any disclaimer, the term of this patent is extended or adjusted under 35 U.S.C. 154(b) by 0 days.

(21) Appl. No.: 09/744,856

(22) PCT Filed: Jul. 23, 1999

(86) PCT No.: PCT/CA99/00673

§ 371 (c)(1),
(2), (4) Date: Apr. 6, 2001

(87) PCT Pub. No.: WO00/07618

PCT Pub. Date: Feb. 17, 2000

(30) Foreign Application Priority Data

Jul. 31, 1998 (CA) .............................................. 2239248

(51) Int. Cl.[7] .......................... C12N 15/00; C12N 7/01; C12N 9/00; C07K 17/00; C07H 21/04
(52) U.S. Cl. ................... 435/69.1; 435/183; 435/235.1; 435/320.1; 530/350; 536/23.1
(58) Field of Search ...................... 514/44, 2; 435/69.1, 435/320.1, 235.1; 536/24.5, 23.1; 530/350; 424/94.1, 183.1

(56) References Cited

FOREIGN PATENT DOCUMENTS

WO          93/19591          10/1993          .......... A01K/63/00

OTHER PUBLICATIONS

Deonarain: Ligand–targeted receptor–mediated vectors for gene delivery. Exp. Opin. Ther. Patents 1998;8:53–69.*
Verma et al: Gene therapy–promises, problems, and prospects. Nature 1997;389:239–242.*
Eck et al: Phar Basis Ther 1995; 77–101.*
McCluskie et al: Mol Med 1999 May;5:287–300.*
Dockrell: J Infection 2001; 42:227–234.*
Brandt et al. (1991). "The herpes simplex virus ribonucleotide reductase is required for ocular virulence", Journal of General Virology, 72:2043–2049.

(List continued on next page.)

*Primary Examiner*—James Ketter
*Assistant Examiner*—Q. Janice Li
(74) *Attorney, Agent, or Firm*—Whyte Hirschboeck Dudek SC

(57) ABSTRACT

An anti-apoptotic agent and a composition derived therefrom, and methods to prevent apoptosis in vivo and in vitro are provided. The anti-apoptotic agent comprises R1 subunit of Herpes simplex virus (HSV) ribonucleotide reductase, or its N-terminal portion of about 350 amino acids. HSV-R1 inhibited TNF-α induced apoptosis, and blocked caspase 8 activation induced by TNF-α and Fas-L expression.

4 Claims, 12 Drawing Sheets

OTHER PUBLICATIONS

Figure 1C:
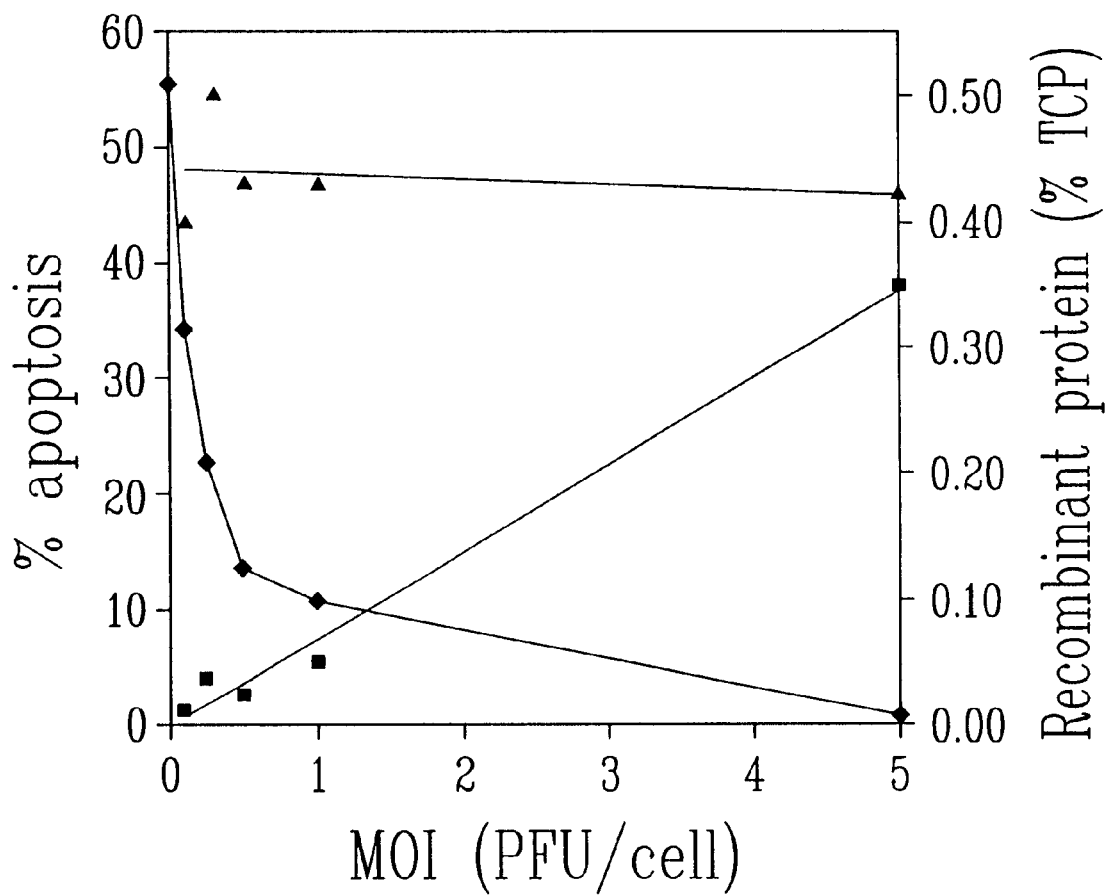

Cameron et al. (1988). "Ribonucleotide Reductase Encoded by Herpes Simplex Virus Is a Determinant of the Pathogenicity of the Virus in Mice and a Valid Antiviral Target". Journal of General Virology, 69:2607–2612.

Chung et al. (1989). "Protein Kinase Activity Associated with the Large Subunit of Herpes Simplex Virus Type 2 Ribonucleotide Reductase (ICP10)". Journal of Virology, 63:3389–3398.

Cohen et al. (1986). "Neutralization of Herpes Simplex Virus Ribonucleotide Reductase Activity by an Oligopeptide–Induced Antiserum Directed against Subunit H2". Journal of Virology, 60: 1130–1133.

Connor, J. (1999). "The unique N terminus of herpes simplex virus type 1 ribonucleotide reductase large subunit is phosphorylated by casein kinase 2, which may have a homologue in *Escherichia coli* ". Jounal of General Virology, 80: 1471–1476.

Conner et al. (1992). "An Autophosphorylating but Not Transphosphorylating Activity Is Associated with the Unique N Terminus of the Herpes Simplex Virus Type 1 Ribonucleotide Reductase Large Subunit". Journal of Virology, 66:7511–7516.

Conner et al. (1994). "Ribonucleotide Reductase of Herpes viruses". Reviews in Medical Virology, 4: 25–34.

Cooper et al. (1995). "Characterization of the Novel Protein Kinase Activity Present in the R1 Subunit of Herpes Simplex Virus Ribonucleotide Reductase". Journal of Virology, 69:4979–4985.

Fawl et al. (1993). "Induction of Reactivation of Herpes Simplex Virus in Murine Sensory Ganglia In Vivo by Cadmium". Journal of Virology, 67: 7025–7031.

Garnier et al. (1994). "Scale–up of the adenovirus expression system for the production of recombinant protein in human 293S cells". Cytotechnology, 15: 145–155.

Goldstein et al. (1988). "Factor(s) Present in Herpes Simplex Virus Type 1–Infected Cells Can Compensate for the Loss of the Large Subunit of the Viral Ribonucleotide Reductase: Characterization of an ICP6 Deletion Mutant". Virology, 166:41–51.

Goldstein et al. (1988). "Herpes Simplex Virus Type 1–Induced Ribonucleotide Reductase Activity Is Dispensable for Virus Growth and DNA Synthesis: Isolation and Characterization of an ICP6 lacZ Insertion Mutant". Journal of Virology, 62: 196–205.

Graham et al. (1977). "Characteristics of a Human Cell Line Transformed by DNA from Human Adenovirus Type 5". J. gen. Virol., 36:59–72.

Halford et al. (1996). "Mechanisms of Herpes Simplex Virus Type 1 Reactivation". Journal of Virology, 70: 5051–5060.

Hunter et al. (1995). "The HSV–2 LA–1 oncoprotein is a member of a novel family of serine/threoinine receptor kinases". International Journal of Oncology, 7: 515–522.

Idowu et al. (1992). "Deletion of the herpes simplex virus type 1 ribonucleotide reductase gene alters virulence and latency in vivo". Antiviral Research, 17: 145–156.

Jacobson et al. (1989). "A Herpes Simplex Virus Ribonucleotide Reductase Deletion Mutant is Defective for Productive Acute and Reactivatable Latent Infections of Mice and for Replication in Mouse Cells". Virology, 173: 276–283.

Jani et al. (1997). "Generation, validation, and large scale production of adenoviral recombinants with large size inserts such as a 6.3 kb human dystrophin cDNA". Journal of Virological Methods, 64:111–124.

Jerome et al. (1998). "Herpes Simplex Virus Type 1 Renders Infected Cells Resistant to Cytotoxic T–Lymphocyte–Induced Apoptosis". Journal of Virology, 72: 436–441.

Jones et al. (1995). "Mutational Analysis of the Herpes Simplex Virus Virion Host Shutoff Protein: Evidence that vhs Functions in the Absence of Other Viral Proteins". Journal of Virology 69: 4863–4871.

Lamarche et al. (1996). "Production of the R2 subunit of ribonucleotide reductase from herpes simplex virus with prokaryotic and eukaryotic expression systems: higher activity of R2 produced by eukaryotic cells related to higher iron–binding capacity". Biochem J., 320: 129–135.

Langelier et al. (1981). "Characterization of Ribonucleotide Reductase Induction in BHK–21/C13 Syrian Hamster Cell Line Upon Infection by Herpes Simplex Virus (HSV)". J. gen. Virol., 57: 21–31.

Langelier et al. (1998). "The R1 Subunit of Herpes Simplex Virus Ribonucleotide Reductase Is a Good Substrate for Host Cell Protein Kinases but Is Not Itself a Protein Kinase". Journal of Biological Chemistry, 273: 1435–1443.

Massie et al. (1998). "New adenovirus vectors for protein production and gene transfer". Cytotechnology, 28: 53–64.

Massie, Bernard et al., Improved Adenovirus Vector Provides Herpes Simplex Virus Ribonucleotide Reductase R1 and R2 Subunits Very Efficiently, Biotechnology, pp. 602–608, vol. 13, Jun. 1995.

Massie, Bernard et al., Inducible Overexpression of a Toxic Protein by an Adenovirus Vector with a Tetracyclin–Regulatable Expression Cassette, Journal of Virology, pp. 2289–2296, Mar. 1998.

Conner, J., et al., Ribonucleotide Reductase of Herpesviruses, Reviews in Medical Virology, vol. 4, pp. 25–34 91994).

Boviatsis, Efstathios J., et al., Antitumor activity and reporter gene transfer into rat brain neoplasms inoculated with herpes simplex virus vectors defective in thymidine kinase or ribonucleotide reductase, Gene Therapy, vol. 1, pp. 323–331 (1994).

Langerlier, Yves, et al., The R1 Subunit of Herpes Simplex Virus Ribonucleotide Reductase is a Good Substrate for Host Cell Protein Kinases but is not Itself a Protein Kinase, The Journal of Biological Chemistry, vol. 273, No. 3, Issue of Jan. 16, pp. 1435–1443, 1998.

* cited by examiner

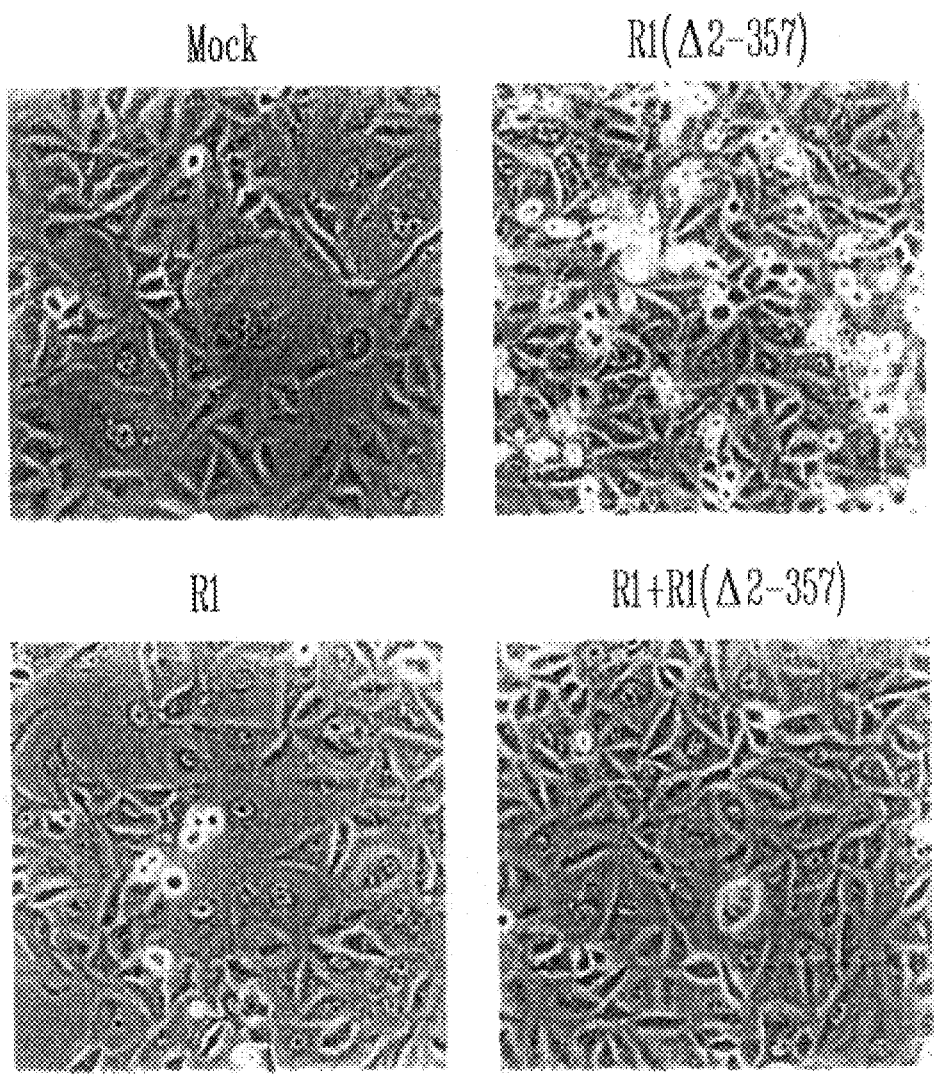
FIG_1A
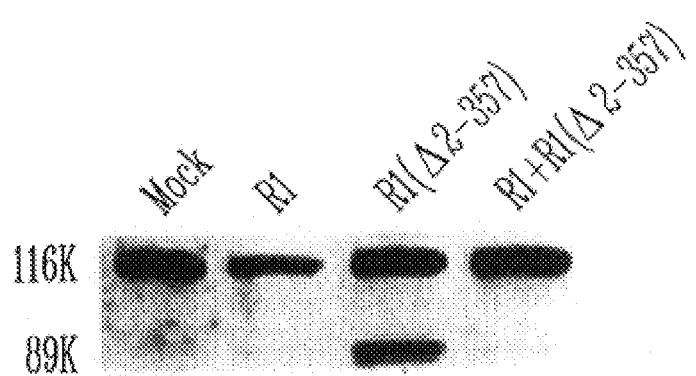
FIG_1B

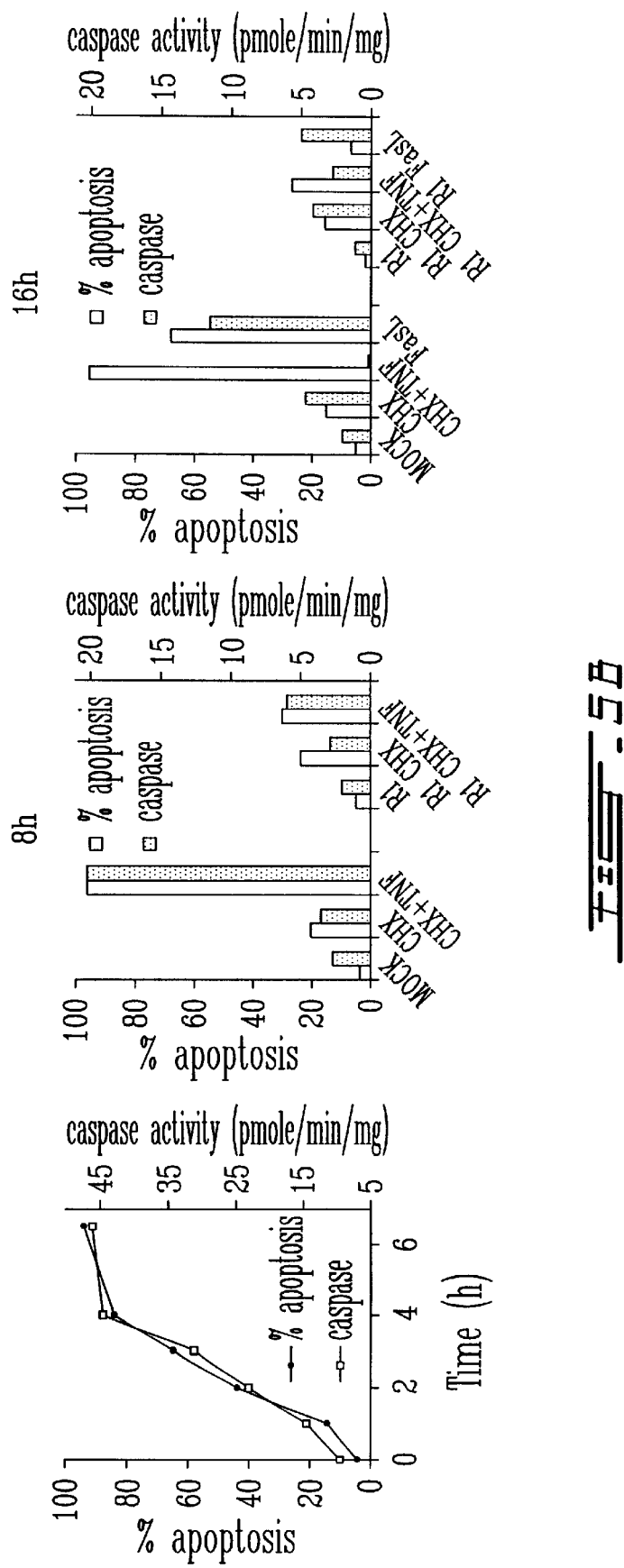

ANTI-APOPTOTIC COMPOSITIONS COMPRISING THE R1 SUBUNIT OF HERPES SIMPLEX VIRUS RIBONUCLEOTIDE REDUCTASE OR ITS N-TERMINAL PORTION; AND USES THEREOF

CROSS-REFERENCE TO RELATED APPLICATIONS

This application claims priority to International Application No PCT/CA99/00673, filed Jul. 23, 1999 (Publ. No. WO 00/07618), and Canadian Application No 2,239,248, filed Jul. 31, 1998.

BACKGROUND OF THE INVENTION

The mechanisms for establishment of latent herpes simplex virus infection in neurons and the subsequent reactivation are very poorly understood. Recent studies have shown that the pattern of gene expression during reactivation is not similar to the one seen in the lytic cycle: the expression of early (E) genes, notably the gene for the subunit 1 (R1) of ribonucleotide reductase, begins several hours before detectable expression of the immediate early (IE) genes (1–3). HSV can be reactivated by numerous stress conditions including NGF deprivation, hyperthermia and cadmium (4) which are also known to induce neuronal cell apoptosis. Therefore, it might be advantageous for the virus to encode protein(s), which are able to block the apoptotic pathways activated by these stimuli. In addition, such proteins could be important to counteract the action of cytotoxic T lymphocytes (CTL) which prevent virus dissemination in cells of the mucosal epithelia where it replicates after being released from neurons (5).

The HSV ribonucleotide reductase converts ribonucleoside diphosphates to the corresponding deoxyribonucleotides and plays a key role in the synthesis of viral DNA (reviewed in (6). The association of two subunits, R1 and R2, the former of which contains the active site, forms the holoenzyme. The R1 subunits of HSV-1 and HSV-2 possess an NH2 domain of about 350 amino acids. This is a unique feature which is not found in R1 of other species, including those of other herpes viruses (7, 8). The role of HSV ribonucleotide reductase has been extensively studied with ribonucleotide reductase null mutants. Studies first done with cultured cells showed that the enzyme is required for efficient replication in non dividing cells. Subsequently, works using animal models demonstrated that the enzyme is required for efficient pathogenicity, is essential for viral reactivation from the neurons, but is not essential for the establishment of latency (9–16). The observations that a mutant virus bearing a deletion of the reductase domain of the R1 gene (hrR3) exhibited the same phenotype in cell culture or in animal models as a virus with a deletion of both the NH2 and the reductase domains (ICP6Δ) has suggested that the NH2 domain may play only a minor role in viral pathogenesis (9, 10, 13). However, as viral mutants which contain deletions only of the R1 NH2 domain have not yet been characterized for their capacity to reactivate, an important role of this domain in HSV reactivation could have been masked by the ribonucleotide reductase deficiency of the two mutants which by itself completely prevents viral replication in the latently infected neurons.

The view that a protein kinase activity or at least an autophosphorylation activity could be intrinsic to the unique NH2 domain of the R1 had been supported over the past ten years by several studies (17–24). However, it has been recently challenged by extensive works showing that R1 does not possess an autophosphorylation activity but rather is a good substrate for copurifying protein kinases (25, 26)]. Our unsuccessful attempts to select standard recombinant Ad for an HSV-2 bearing a complete deletion of its NH2 domain, ΔR1, have led us to suspect that this protein could be cytotoxic and thus, to develop a transfer vector (pAdTR5) that utilizes a tetracycline-regulated expression cassette. Hence, a recombinant Ad with tetracycline-regulated expression of ΔR1, Ad5TR5-R1 (Δ2–357), was readily obtained and the pro-apoptotic potential of the ΔR1 protein was demonstrated by infecting cells expressing the tet-regulated transactivator (tTA) (27). This is therefore a strong suggestion that the N-terminal fragment of the R1 protein is an anti-apoptotic protein per se. A broad anti-apoptotic activity would make the N-terminal R1 protein a candidate of choice as an anti-apoptotic agent, alone or in combination with other anti-apoptotic agents.

The anti-apoptotic activity of the RI protein N-terminal domain is exploitable per se, as well as in the making of a virus or of a viral vector that would be less virulent. The "cassette" RI N-terminal would therefore be inserted in such a virus or viral vector. On the opposite a herpes virus encoding the RI without the anti-apoptotic domain could be used to destroy undesirable cells like cancer cells. In both cases, gene therapy is envisaged to deliver one or the other RI proteins as well as to co-deliver other proteins of interest.

SUMMARY OF THE INVENTION

The R1 subunit of herpes simplex virus (HSV) ribonucleotide reductase, which is expressed very early after viral reactivation, possesses an N-terminal domain of about 350 amino acids of unknown function. Using an adenovirus (Ad) inducible system we had demonstrated that a complete deletion of this domain produces a cytotoxic protein. We now report that apoptotic death induced by this trncated R1 could be completely prevented by coexpression of the full-length R1. The R1 anti-apoptotic activity was further substantiated by showing that expression of this protein at low level can completely block apoptosis induced either by TNF-receptor family triggering in the presence of cycloheximide (CHX) or by Fas-L coexpression with an Ad recombinant. In both cases, the protection was lost when inhibiting tTA function with the tetrycline analog doxycycline shut down R1 expression. A level of R1 of 0.005% total cell protein was sufficient for half-maximal protection against TNFα+CHX. By monitoring caspase 8 activation either by immunoblot with an antiserum visualizing the inactive 56-kDa proform and the active 18-kDa species or by an in vitro assay using ETD-AFC as caspase 8 specific fluorescent substrate, we found that the strong activation of caspase 8 induced either by TNF-α+CHX or Fas-L expression was prevented by the R1 protein. Finally, using an HSV-1 R1 deletion mutant, ICP6Δ, we obtained direct evidence for the importance of HSV-R1 in protecting HSV-infected cells against cytokine-induced apoptosis. These results show that, in addition to its reductase function which is essential for viral reactivation, the HSV R1 could contribute to viral propagation by preventing apoptosis induced by the immune system. The N-terminal domain by itself is as anti-apoptotic as the whole R1 protein. An anti-apoptotic agent and a composition derived therefrom are described and claimed.

The present invention relates to the new use of the subunit 1 of HSV ribonucleotide (RI) reductase, a variant or a part thereof having a functional anti-apoptotic N-terminal domain, as an anti-apoptotic agent.

The present invention further relates to an anti-apoptotic agent comprising the N-terminal 357 amino acids of the RI sub-unit, a variant thereof or anti-apoptotic part thereof. It is another object of this invention to provide an anti-apoptotic composition comprising RI, the N-terminal portion of RI, a variant or a part thereof having an anti-apoptotic activity. A variant is defined as a molecule having been subjected to mutation by substitution, deletion or addition, which mutation has no deleterious effect on the anti-apoptotic activities. The sequences of the RI subunit of HSV-1 and -2 are disclosed in (7–8). Similarity or identity of more than 50%, preferably of more than 70%, even more preferably of more than 90%, would achieve a functional variant provided that the mutation is not directed to an amino acid residue essential for the activity. Due to codon degenerescence, a lesser degree of conservation is needed for the nucleic acids used for the purpose of providing functional variants.

Such a composition may also comprise another anti-apoptotic agent. Such agent includes but is not limited to anti-caspase molecules (such as enzymatic inhibitors, inhibitors of synthesis or activation, antibodies or other ligands), anti-cytokines such as anti-TNFα molecules (antagonists, degradation activators or inhibitors of synthesis or of secretion, antibodies or other ligands), a bcl-2 protein, homologue or mimetic, anti-Fas-L molecules (antagonists, degradation activators, or inhibitors of synthesis or of secretion), and agents interfering with the recruitment, binding and/or activity of cytotoxic white blood cells at a diseased tissue site.

We demonstrated, by coinfection experiments with full-length R1 and ΔR1 recombinants to obtain coexpression of both proteins, that the NH2 domain of the HSV-R1 has an antiapoptotic function able to protect the cells against death triggered by the expression of the reductase domain alone. More importantly, it was found that the full-length R1 has a broad anti-apoptotic potential as it is able to protect cells against not only ΔR1 but also against death induced by TNF-α and Fas receptor triggering. Caspase 8 activation, which occurs with both types of death-inducing signal, was impaired by R1 expression. Finally, using an HSV-1 R1 deletion mutant, ICP6Δ, we obtained direct evidence for the importance of HSV-R1 in protecting HSV-infected cells against cytokine-induced apoptosis.

DESCRIPTION OF THE PREFERRED EMBODIMENT OF THE INVENTION

The objects, advantages and other features of the present invention will become more apparent upon reading of the following non restrictive description of preferred embodiments thereof, given by way of example only with reference to the accompanying drawings.

FIGS. 1A–1C. Full-length R1 prevents apoptosis induced by R1 (Δ2–357). (A)A549-tTA cells were mock-infected (Mock), infected for 18 h at an MOI of 5 PFU/cell with Ad5TR5-R1(Δ2–357) (R1 (Δ2–357)), with Ad5TR5-R1 (R1), or infected during the first 7 h with Ad5TR5-R1 and then with Ad5TR5-R1 (Δ2–357) (R1+R1 (Δ2–357)). (B) Cell lysates were prepared from the cell populations described in A and analyzed for PARP (116K) cleavage by immunoblotting. (C) A549-tTA cells were first infected with increasing MOIs of Ad5TR5R1 and reinfected 7 h later with Ad5TR5R1(Δ2–357) at an MOI of 5 PFU. The percentage of detached cells was evaluated from 24 to 26 h after the first infection using method 2 described in Material and Methods (♦). Accumulation of R1(Δ2–357) (▲) and full-length R1 (■) was quantified respectively by Coomassie blue gel staining and by immunoblotting using purified HSV-2 R1 as standard and the results are expressed as percentage of total cell protein (TCP).

Figure 2A:
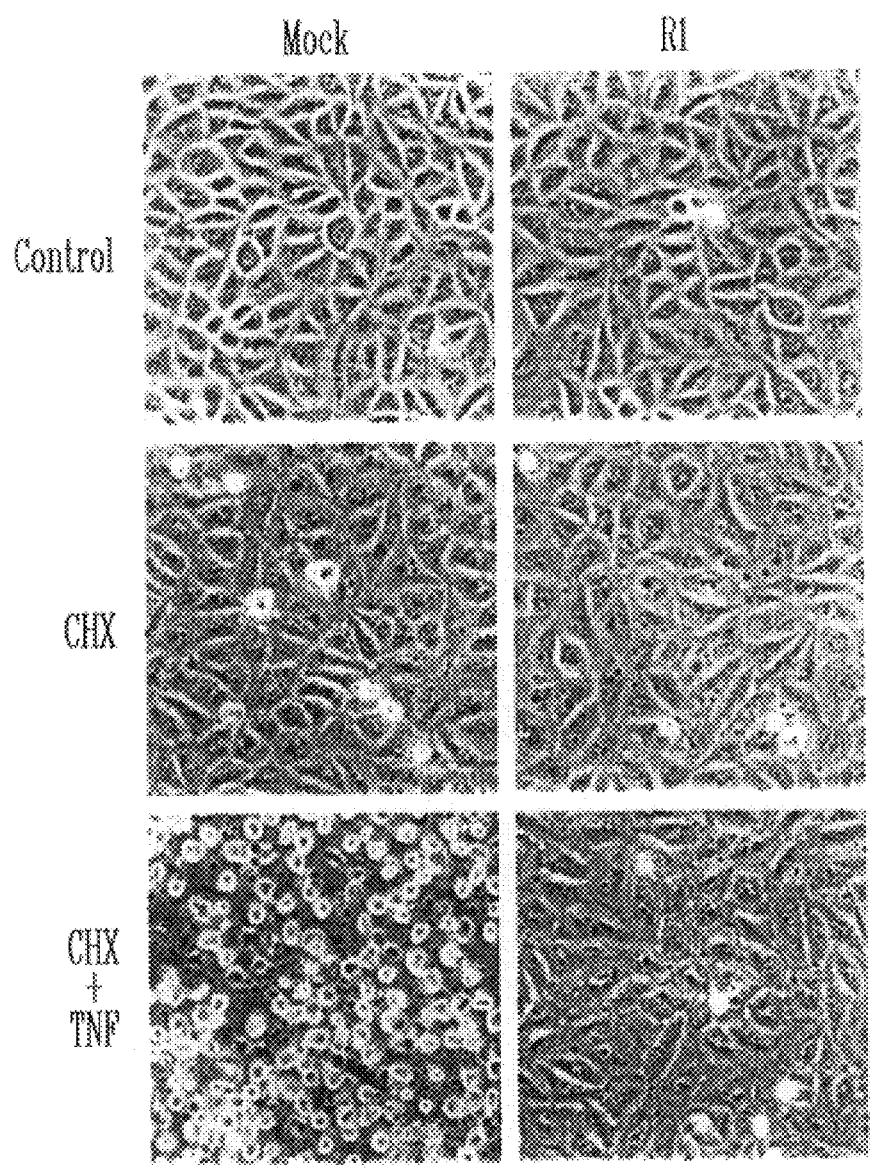
Figure 2B:
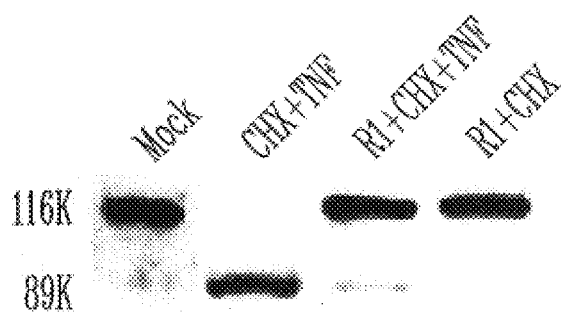

FIG. 2. Full-length R1 inhibits TNFα-induced apoptosis's apoptotic-inducing agent. (A) Morphological appearance of cells photographed using a phase-contrast microscope. A549-tTA cells were infected with Ad5TR5-R1 (R1) at an MOI of 10 or mock-infected (Mock). The cells received 7 h later either control medium (Control or medium containing 30 μg/ml (CHX) or 30 μg/ml CHX plus 2,5 ng/ml TNF-α (CHX+TNF) and were photographed 18 h later. (B) Cell lysates were prepared from the cell populations described in A and analyzed for PARP (116K) cleavage by immunoblotting. (C) A549-tTA cells were infected with increasing MOIs of Ad5TR5-R1 (■,□) or Ad5TR5GFP (Δ) and received 7 h later CHX (□) or CHX+TNF (■); mock-infected untreated control (○). The percentage of apoptosis was evaluated from 24 to 26 h after the first infection by counting under microscopic observation apoptotic and non-apoptotic cells (method 1 in material and methods). The dashed line (right axis) represents the percentage of cells expected to be infected by the Ad recombinant according to the Poisson distribution.

Figure 2C:
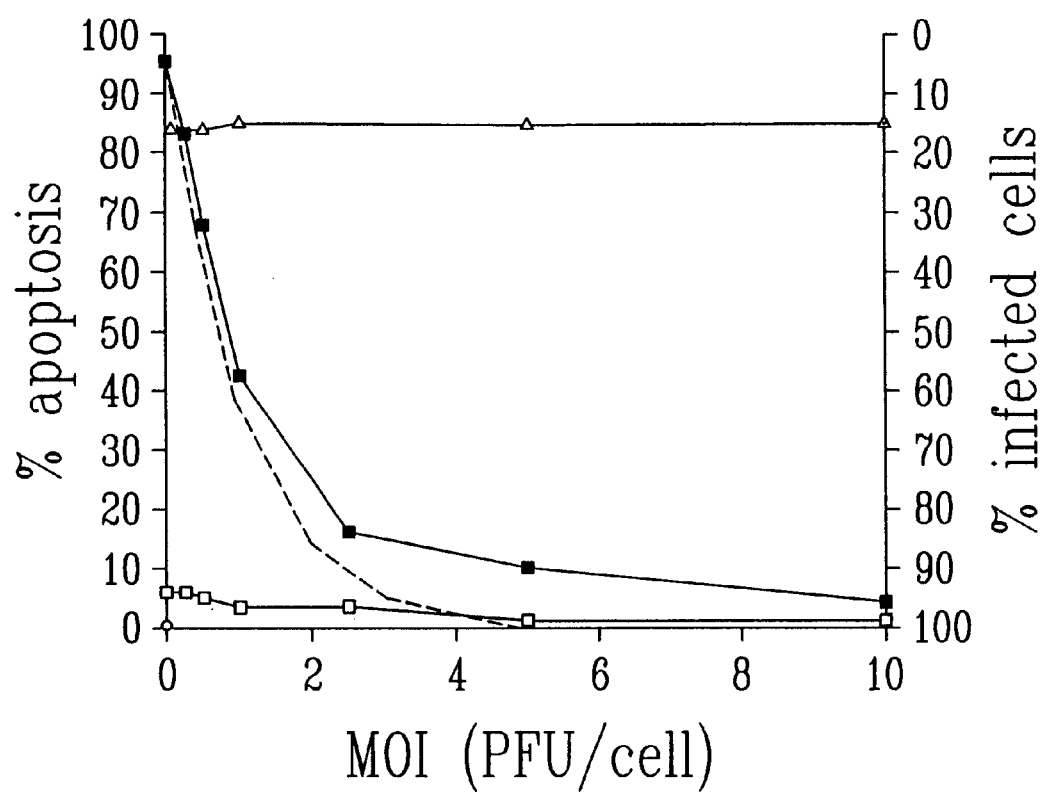
Figure 3A:
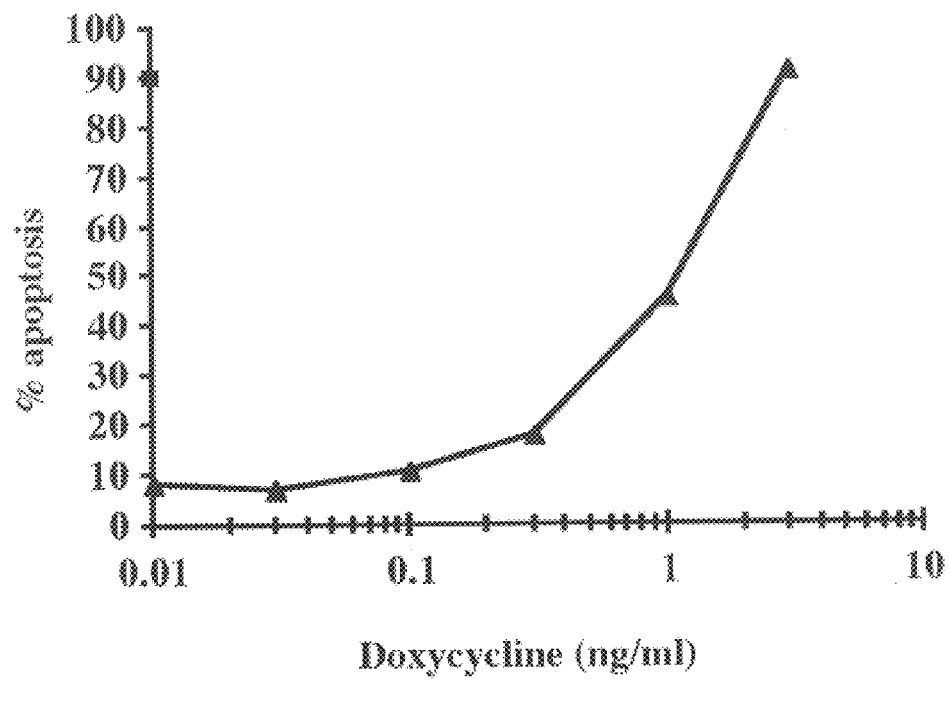
Figure 3B:
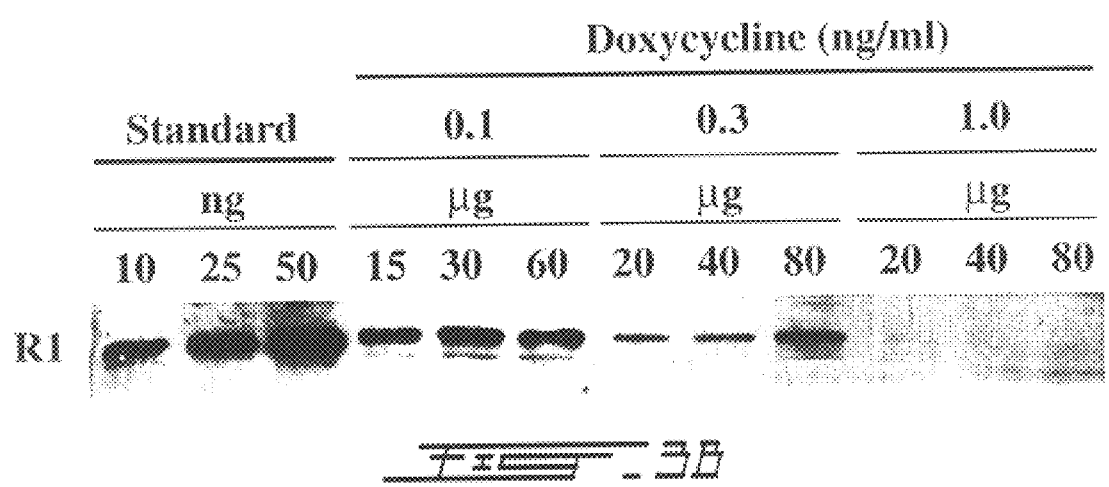

FIG. 3. Doxycycline decreases R1 accumulation and R1-protection against TNF-α (A) A549-tTA cells were infected with Ad5TR5-R1 at an MOI of 5 in the presence of increasing concentrations of doxycycline (▲) or mock-infected (■) and received 7 h later CHX+TNF. The percentage of apoptosis was evaluated at 24 h pi as indicated in FIG. 2C. (B) Increasing amounts of proteins extracted from harvested cells were immunoblotted with an anti R1 serum and a representative experiment is shown. Quantification was performed by densitometric comparison with purified R1 standard. From 3 independent blots, the calculated mean values expressed in percentage of TCP for the 0.1, 0.3 and 1.0 ng/ml doxycycline samples were respectively 0.05%, 0.006% and >0.001%.

Figure 4A:
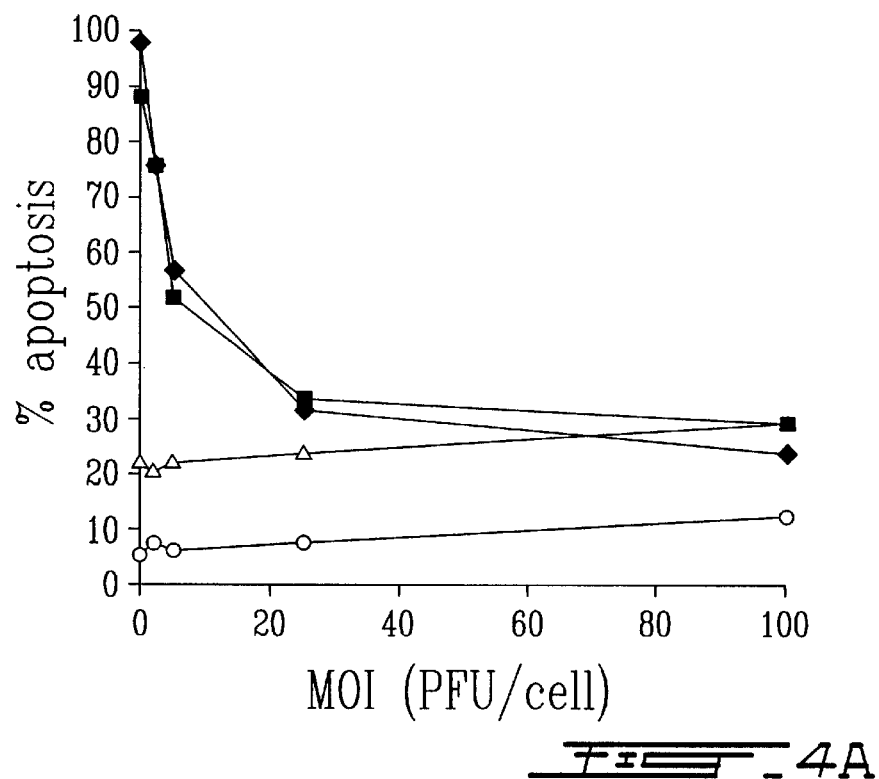

FIG. 4. Protection against TNF-α and Fas is independent of the tTA or rtTA proteins and of the presence of CHX. (A) HeLa cells were infected with increasing MOIs of Ad5CMV5-R1 and received 7 h later control medium (○) or medium containing CHX (Δ), or CHX+TNF (■) or anti-Fas antiserum (♦) and apoptosis was scored from 24 to 26 h pi, (B) A549-tTA cells were first infected with Ad5TR5-R1 at an MOI of 10 in the absence (Δ, ×) or the presence (●) of doxycycline or mock-infected (■, □). They were reinfected (Δ, ●, ■) or not (×) 7 h later with Ad5CMV-Fas-L at an MOI of 10. Apoptosis was scored as described in FIG. 2C at the indicated times after Ad5TR5-R1 infection.

FIG. 5. HSV-R1 impairs caspase 8 activation. A549-tTA cells were either mock-infected (MOCK) or infected with the recombinant Ad5TR5-R1 (R1) at an MOI of 5 for 7 h before the addition of CHX (CHX), CHX+TNFα (CHX+ TNF), no addition (Control) or reinfection with Ad5CMV-Fas-L at an MOI of 25. After 8 h (8 h), 16 h (16 h) or at the indicated time in the time-course experiment, apoptosis was scored as described in FIG. 2C, cells were harvested and cytoplasmic extracts were prepared for caspase 8 determination as described in material and methods. Caspase 8 activation was monitored either in panel (A) by immunoblotting 20 μg of protein extract with the caspase 8 antiserum or in panel (B) by measuring caspase 8 activity by incubating 60 μg of protein extract with IETD-AFC as caspase 8 specific substrate.

Figure 6:
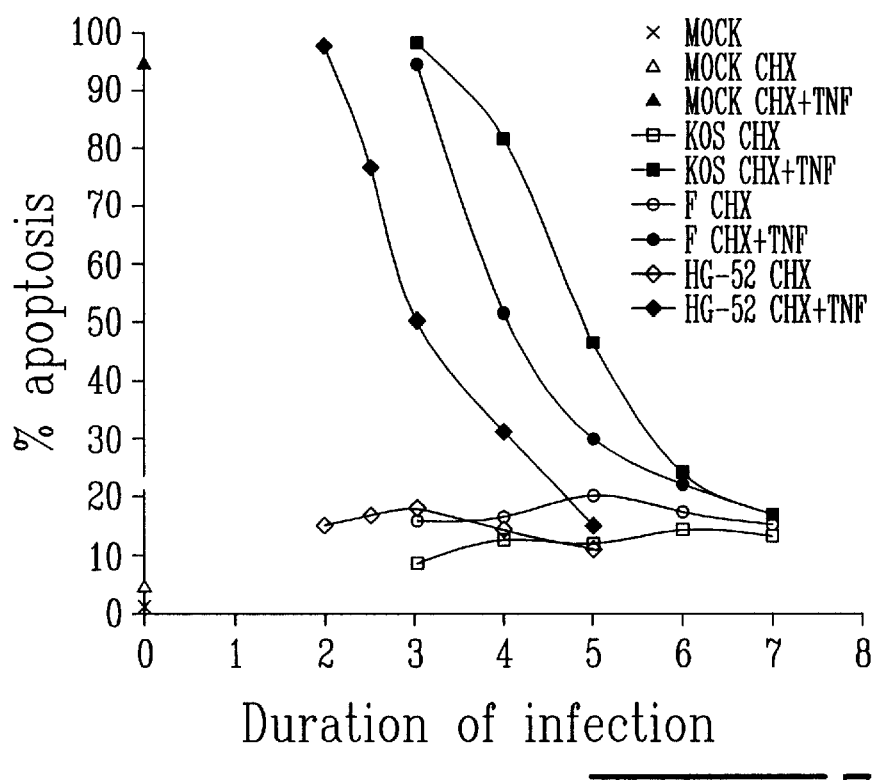

FIG. 6. HSV infection protects A549-tTA cells against TNF-α induced apoptosis. A549-tTA cells were mock-infected (*, Δ,▲) or infected with either the HSV-1 strains KOS (□,■) and F (○,●) or the HSV-2 strain HG-52 (◇,◆) at MOIs of 10 for increasing periods before the addition of either CHX (Δ,□,○,◇), CHX+TNFα (▲,■,●,◆) or control medium (*). Apoptosis was scored, as indicated in FIG. 2C, 20 h after the addition of the lethal cocktail.

Figure 7:
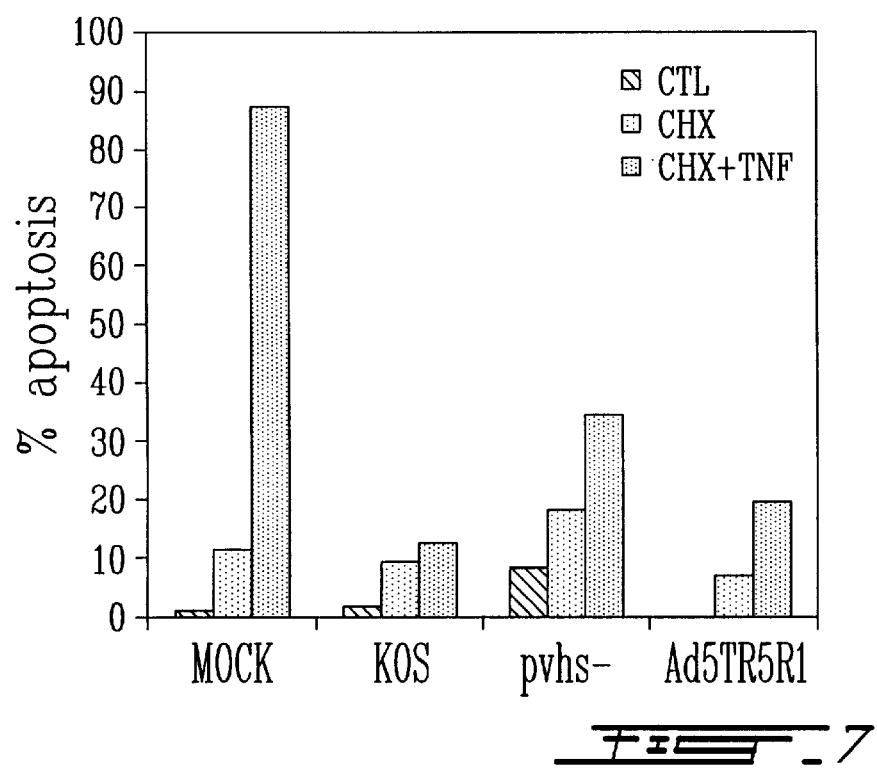

FIG. 7. The vhs mutant pvhs– has a reduced anti-apoptotic potential against TNF-α. A549-tTA cells were mock-infected (Mock), infected with either the parental HSV-1 KOS (KOS) or the null vhs mutant pvhs– (pvhs–) at an MOI of 10 or infected with Ad5TR5-R1 (Ad5TR5R1) at an MOI of 5 for 7 h before the addition of CHX+TNFα. Apoptosis was scored 20 h after the addition of the lethal cocktail as described in FIG. 2C.

FIG. 8. The R1 mutant ICP6Δ has a reduced anti-apoptotic potential against TNF-α. A549-tTA cells were either mock-infected (MOCK) or infected with increasing MOIs of either the parental HSV-1 KOS (KOS) or the R1 null mutant ICP6Δ (ICP6Δ) for 7 h before the addition of either control medium (Control), CHX (CHX), or CHX+ TNFα (CHX+TNF). (A) Apoptosis was scored 20 h after the addition of the lethal cocktail as described in FIG. 2C. (B) PARP cleavage and R2 protein were detected by immunoblotting of protein extracts prepared at 20 h pi.

Figure 9:
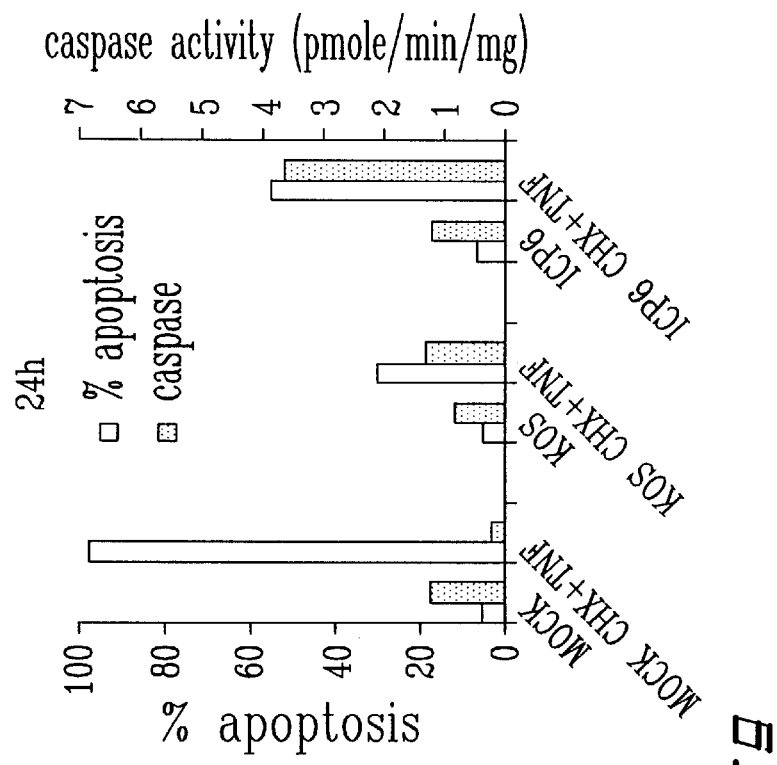
Figure 9:
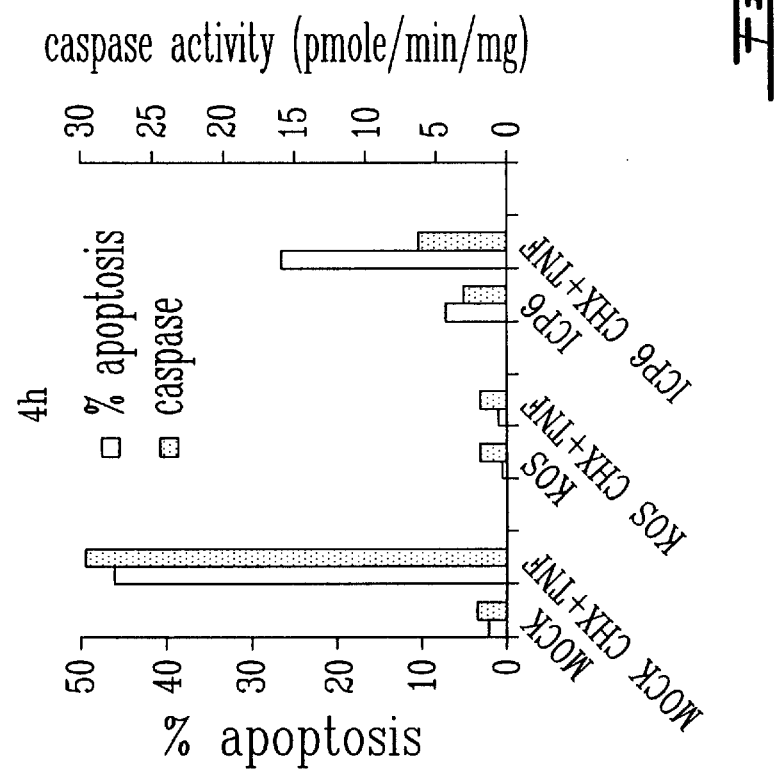

FIG. 9. The R1 mutant ICP6Δ is defective in blocking TNF-induced caspase 8 activation. A549-tTA cells were either mock-infected (MOCK) or infected at an MOI of 10 with either the parental HSV-1 KOS (KOS) or the R1 null mutant ICP6Δ (ICP6Δ) for 8 h before the addition or not of CHX+TNFα (CHX+TNF). % apoptosis and caspase 8 activity were measured at 4 h and 24 h after the addition of the lethal cocktail as described in FIG. 5.

MATERIALS AND METHODS

Cells, recombinant Ad and HSV. The conditions for the culture of human 293 cells, either the original anchorage dependent 293A line (29) or 293S, an anchorage independent clone, were as described (29, 30). HeLa S3 and A549 cells were obtained from ATCC and cultured with the same medium as for 293A cells. To complement the tet-regulated expression cassette, clones expressing tTA or rtTA transactivators were derived from A549 and HeLa S3 cells. Using a tet-regulated reporter gene, A549-tTA or HeLa-rtTA cell lines were further selected for their ability to retain both high and inducible levels of expression as described recently (27). They were maintained in medium respectively containing 30 μg/ml phleomycin or 30 μg/ml hygromycin until one passage before the experiments.

The recombinants Ad5TR5-R1 and Ad5CMV5-R1 for the expression of the R1 subunit of the HSV-2 ribonucleotide reductase and Ad5TR5-R1(Δ2–357), an Ad recombinant expressing a truncated R1, were constructed as recently described (27). The construction of Ad5CMV-Fas-L, a recombinant expressing the rat Fas-L under the control of the CMV IE promoter, was done using the standard protocol detailed in Jani et al. (1997) (31). Large scale virus stocks which did not contain more than 1 replication-competent Ad/$10^7$ PFU were prepared by infecting $3\times10^9$ 293S cells in suspension culture and titered by plaque assay on 293A cells as recently detailed (32). The adsorption conditions for infection and titration were based on the protocol described by (33) to insure optimal entry of the virus. Briefly, minimal volume of virus suspension (ex., 1.0 ml in 60 mm dishes) was incubated with cells with continuous agitation on a rocker for 7 h to 16 h. High titer stocks of HSV-1 (strain F) and HSV-2 (strain HG-52) were prepared by infecting confluent BHK-21/C13 cells with a low multiplicity of infection (MOI) as previously described (34). The ribonucleotide reductase null HSV-1 mutant ICP-6Δ (9) kindly provided by Sandra Weller and its parental strain KOS were propagated and titered on subconfluent Vero cells. The stock of pvhs⁻, an HSV-1 deletion mutant of the viral host shut off gene derived from the KOS strain (35), was kindly provided by James Smiley. Apoptosis assays. Cells were usually seeded 2 days before infection in 60 mm Petri dishes at $1\times10^6$ cells/dish. The Ad recombinants Ad5TR5-R1 (Δ2–357) or Ad5CMV-Fas-L suspended in 1.0 ml of medium were adsorbed onto the cells for 18 h. For the coinfection experiments with Ad5TR5-R1 or Ad5CMV5-R1, the recombinants were first adsorbed onto the cells for 7 h. The HSV suspended in 0.5 ml of medium containing 2% fetal calf serum (2% FCS) were adsorbed onto the cells for 1h after that period, the medium was replaced by 2 ml of fresh 2% FCS medium.

As normal A549-tTA cells exhibit a flat morphology and are strongly adherent to Petri dishes, they can be easily distinguished from cells exhibiting apoptotic morphology which is characterized by membrane blebbing, pyknosis and cell body condensation. Soon after their rounding, the apoptotic cells detached from the substratum and can be seen floating in the medium. Two methods were used to determine the percentage of apoptotic cells. 1) The detached cells which had a strong tendency to aggregate were first dispersed by gently pipetting the medium and the cells seen in at least 3 random-selected fields were counted in each duplicate dish using a Nikon Diaphot inverted photomicroscope (200×). The percentage of apoptotic cells was evaluated by dividing the number of cells with apoptotic morphology by the total number of cells. This first method was used in all the experiments with HSV infection as it permits to distinguish apoptosis from cell rounding or syncitium formation induced by these viruses. 2) The detached cells contained in the culture medium and in a 5 ml PBS washing of the dish were centrifuged and resuspended in a volume of PBS appropriate for counting with a hemacytometer. The attached cells were counted similarly after trypsinization. The percentage of apoptotic cells in duplicate dishes was evaluated by dividing the number of detached cells by the total number of cells (detached+attached). For protein analysis, immediately after their counting the cells were washed in PBS resuspended in the appropriate buffer and frozen at –80° C. until extraction.

For the experiments where apoptosis was induced by cycloheximide (30 μg/ml) plus either human recombinant TNFα (2.5 ng/ml) obtained from Signia or anti-human Fas mAb CH-11 (50 ng/ml) obtained from Upstate biotechnology, cells were usually plated the day before infection Doxycycline when used to inhibit the recombinant protein synthesis was added at 30 ng/ml throughout the duration of the experiment and at 3 μg/ml to induce protein expression. For DNA and protein analysis, the cells were scraped in the medium with a rubber polieman, washed with PBS resuspended respectively in 50 mM Tns-Hcl (ph 8.0), SDS 2%, 20 mM EDTA or in 80 mM Tris-HCl (pH 6.8). SDS 2% 6 M urea and frozen at –80° C. until extraction.

Analysis of DNA laddering by agarose gel electrophoresis Cellular DNA was extracted by the salting out procedure. Electrophoresis was. done with 1.2% agarose gel in Tns-borate buffer pH 8.0 containing 0.1% SDS (w/v) overnight at 50 volts. DNA was visualized under UV illumination after staining with ethidium bromide Protein extraction for SDS-PAGE or Western blot analyses. Total protein extracts were prepared by lysing cells in protein extraction buffer followed by sonication to shear the DNA. After determination of protein concentration using the Bio-Rad DC (Detergent Compatible) colorimeric assay with BSA as standard, DTT was added to a concentration of 5% (V/V) and the samples were boiled for 5 min before performing SDS-PAGE and Western blotting as described previously (36). Quantification of the percentage of recombinant protein in total protein extracts was done by densitometric scanning of the lanes of Coomassie blue stained gels with an imager system (Canberra Packard) as detailed previously (36) or by Western blotting. Following incubation within an appropriate primary antibody, the Western blotted membrane was incubated with horseradish peroxidane-conjugated goat anti-rabbit antibody (Amersham Corp., Arlington Heights, Ill.) or horseradish peroxidase-conjugated goat anti-rabbit antibody with horseradish peroxidase-conjugated goat anti-mouse lgG (Jackson ImmunoResearch Laboratories, Inc.) and the bound peroxidase was revealed either by ECL (Amersham) or SuperSignal™ (Pierce) detector reagents. For HSV R1 detection, 18R1 a rabbit polyclonal anti-R1 antiserum was used; for HSV R2, P9, a polyclonal antiserum directed against the HSV R2 carpoxy-terminus (37); for caspase 8, mAD C15 a mouse monoclonal Ab kindly provided by Marcus Peter: for poly (ADP-nbose) polymerase (PARP), PARP (Ab-2) a mouse monoclonal Ab generated by immunization on with purified calf thymus PARP (Calbiochem). In vitro caspase assays. The ApoAlert™ caspase 8 fluorescent assay kit (Clontech) was used to measure caspase 8 activity. Cytoplasmic extracts obtained by incubating cells in ice-cold cell lysis buffer for 10 min followed by centrifugation at 12,000 rpm in a microcentrifuge for 3 min. The enzymatic activity was determined using a 96-micro well plate to incubate at 37° C. mixtures of 50 pg of protein with reaction buffer and 50 $\mu$M IEDT-AFC conjugated substrate (100 $\mu$l/reaction). The initial rate of release of free AFC was monitored with a 96-well plate fluorometer using a 450-nm excitation filter and 530-nm emission filter. Quantification of free AFC was performed using the AFC standard provided with the kit.

RESULTS

Full-length R1 protects cells against the pro-apoptotic action of R1 ($\Delta$2–357). In previous works, we had observed that infection of A549-tTA cells with Ad5TR5-R1($\Delta$2–357), an Ad recombinant which inducibly express an HSV ribonucleotide reductase R1 subunit deleted of its unique amino-terminal domain, produced cell death (27). Hence, we recently found that the death of A549-tTA or HeLa-rtTA cells infected by Ad5TR5-R1(A2–357) exhibited hallmarks of apoptosis: cytoplasmic blebbing, cell rounding and detachment, cleavage of PARP, caspase 3 activation and DNA laddering. Additional evidence for an apoptotic process came from the observation that coinfection with an Ad recombinant expressing the anti-apoptotic E1B 19K Ad protein (a bcl-2 homologue) completely abrogates apoptosis.

One obvious possibility raised by these observations is that the HSV-R1 NH2 domain has an anti-apoptotic function able to protect the cells against death triggered by the expression of the reductase domain alone. To test that hypothesis, cells were coinfected with full-length and truncated R1 ($\Delta$R1) recombinants to obtain coexpression of both proteins. As shown in FIG. 1, when the A549-tTA cells were first infected with Ad5TR5-R1 at an MOI of 5 followed 7 h later by a second infection with 5 PFU of Ad5TR5-R1 ($\Delta$2–357), the full-length protein efficiently prevent the morphological changes (A) and PARP degradation (B) induced by $\Delta$R1. By varying the MOI of Ad5TR5-R1 and scoring the extent of apoptosis by quantifying the percentage of cells exhibiting apoptotic morphology, it was possible to demonstrate that infection by only one Ad5TR5-R1 recombinant virion was sufficient to confer protection against apoptotic death (C). Indeed, the curve showing the decrease in the percentage of detached cells as a function of the MOI was superimposable with the curse of the percentage of cells expected to be infected by the Ad recombinant according to the Poisson distribution (not shown). Precise quantification of both proteins revealed that the synthesis of the full-length R1 protein did not alter the one of the $\Delta$R1 protein (C), ruling out the possibility that the protection was the result of a decrease in the AR1 synthesis. Moreover, nearly maximal protection was attained with an amount of R1 much lower than the amount of $\Delta$R1 (8 fold lower at 1 PFU), suggesting that the protection was not due to the formation of non-apoptotic heterodimers.

Full-length R1 inhibits TNF-$\alpha$-induced apotosis. To further explore the protective role of the full-length HSV-R1, two other related pro-apoptotic stimuli (apoptotic-inducing agent) were tested. A549-tTA cells massively undergo apoptosis when exposed to TNF-$\alpha$ in presence of cycloheximide (CHX), more than 90% of the cells being seen floating in the medium 18 h after the treatment. In contrast, no more than 5% of the cells that had been infected with Ad5TR5-R1 for 7 h prior to the application of the pro-apoptotic stimulus exhibited apoptotic morphological appearance (FIG. 2 A). Similar results were obtained with HeLa-rtTA cells when they were infected in presence of doxycyline to induce R1 expression (data not shown). The protection conferred to A549-tTA cells by Ad5TR5-R1 infection was confirmed by the observation that the TNF-$\alpha$ induced PARP cleavage was completely prevented in infected cells (FIG. 2 B). Moreover, as shown in FIG. 2C, the curve showing the decrease in the percentage of apoptotic cells as a function of the MOI of Ad5TR5-R1 was nearly superimposable with the curve of the percentage of cells expected to be infected by the Ad recombinant according to the Poisson distribution. Once again, this result indicates that infection by only one Ad recombinant virion was sufficient to confer protection against TNF-$\alpha$.

Evidence that R1 expression is necessary to the protective effect came from the observations that infection with Ad5TR5-R1 in presence of 30 ng/ml doxycycline or with Ad5TR5-GFP did not confer protection. To determine the minimal amount of R1 necessary for protection, A549tTA cells were infected at 5.0 PFU/cell in the presence of increasing concentrations of doxycycline (FIG. 3). Quantification of the R1 concentration by immunoblotting using purified R1 as standard (B) revealed that a doxycycline concentration of 0,3 ng/ml, which reduced only slightly the level of protection, decreased the R1 concentration to 0,006% TCP (A). This concentration is about 150 fold lower than the one that maximally accumulated in HSV-1 infected cells and can be detected in as early as 2 h after infection.

Even if at the low MOI used in the above experiments the level of expression of Ad genes should be extremely low due to the absence of Ad replication, the involvement of Ad protein(s) in the protective effect even if highly unlikely could not be completely ruled out. To verify this possibility, pAd5TR5-R1, the shuttle plasmid used to construct the Ad recombinant and, as negative control, pAd5TR5, were transfected in HeLa-rtTA cells. As only the transfection with the R1 expressing plasmid increased the survival of TNF+CHX-treated cells and as this protection was abolished in the absence of doxycycline (data not shown), we could conclude that the R1 protective activity does not necessitate the co-expression of any Ad protein.

R1 NH2 domain is sufficient for protection against TNF-α. To determine whether the antiapoptotic function of the R1 protein necessitates the association of its NH2 domain with the reductase domain, the first 398 amino acids of the HSV-2 R1 were transiently expressed from the shuttle plasmid pAdTR5-R1 (A399–1144)-K7-GFP$_Q$ for 18 h before treatment of the cells with TNF-α+CHX. As the protection obtained with the NH2 domain alone was as good as the one obtained in parallel transfection with pAdTR5R1-K7-GFP$_Q$, a control plasmid expressing the fullength R1, we could conclude that this domain is sufficient to protect cells against TNF-α (Table 1).

Full-length R1 inhibits Fas receptor-induced apoptosis. Fas activation induced by adding to the culture medium the anti-Fas antibody CH 11 in presence of CHX was as effective as TNF-α in mediating apoptosis with HeLa-rtTA or parental HeLa cells but was less potent with A549tTA cells, only 35% of the cells being scored apoptotic at 48 h. Ad5TR5-R1 infection of HeLa-rtTA and A549-tTA cells blocked Fas receptor-induced apoptosis as efficiently as it did in TNFα-treated cells (data not shown).

To rule out the possible involvement of the tTA protein in the protective effect of the full-length R1, HeLa cells were infected with the recombinant Ad5CMV5-R1, a constitutive Ad with an improved CMV-based expression cassette. The results shown in FIG. 4A indicated that full protection could also be obtained in these cells against both pro-apoptotic stimuli. As predicted from our previous observation that Ad5CMV5-R1 at low MOIs yielded lower expression level than Ad5TR5-R1 (27), a higher MOI of 25 was necessary for full protection. Quantification of the R1 amount in these Ad5CMV5-R1 infected cells (0,005%) revealed that it was similar to the R1 minimal amount found in nearly fully protected tTA-expressing cells (0,006%). This result demonstrates that the presence of the tTA protein is not necessary to the R1 anti-apoptotic activity.

Figure 4B:
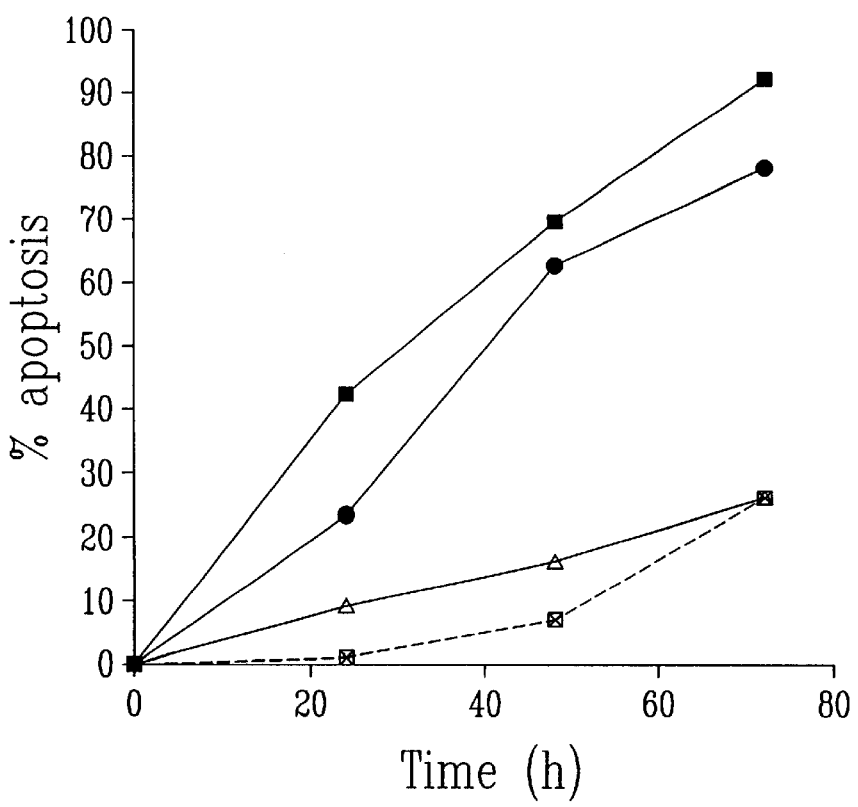

Finally, to determine whether protection could be observed in conditions where apoptosis was induced in more physiological conditions (without CHX), Ad5CMV-Fas-L, an Ad recombinant which express Fas-L under the control of the standard CMV promoter, was used. At 72 h post infection with this recombinant, apoptosis occurred in more than 90% of A549-tTA cells but when they had been pre-infected for 7 h with Ad5TR5-R1, they were efficiently protected, the level of apoptosis being equal to the one seen in mock-infected control (FIG. 4B). Adding doxycyline throughout the infection considerably reduced the protection. Altogether these results demonstrate that the HSV-R1 is able to protect cells against apoptosis induced by the activation of death receptors.

HSV R1 blocks caspase 8 activation induced by TNF-α and Fas-L. Apoptosis induction by activation of TNF-receptor superfamily involved the assemblage of a protein-signalling complex that necessitates the physical interaction of caspases (8 and 10) followed by their activation. Indication that HSV-2 R1 could act in pathway specific to receptor induced apoptosis came first from the observations that the protein was unable to protect cells against apoptosis induced by DNA replication stalling by inhibiting ribonucleotide reductase with dATP+deoxycoformycin (data not shown).

Figure 5A:
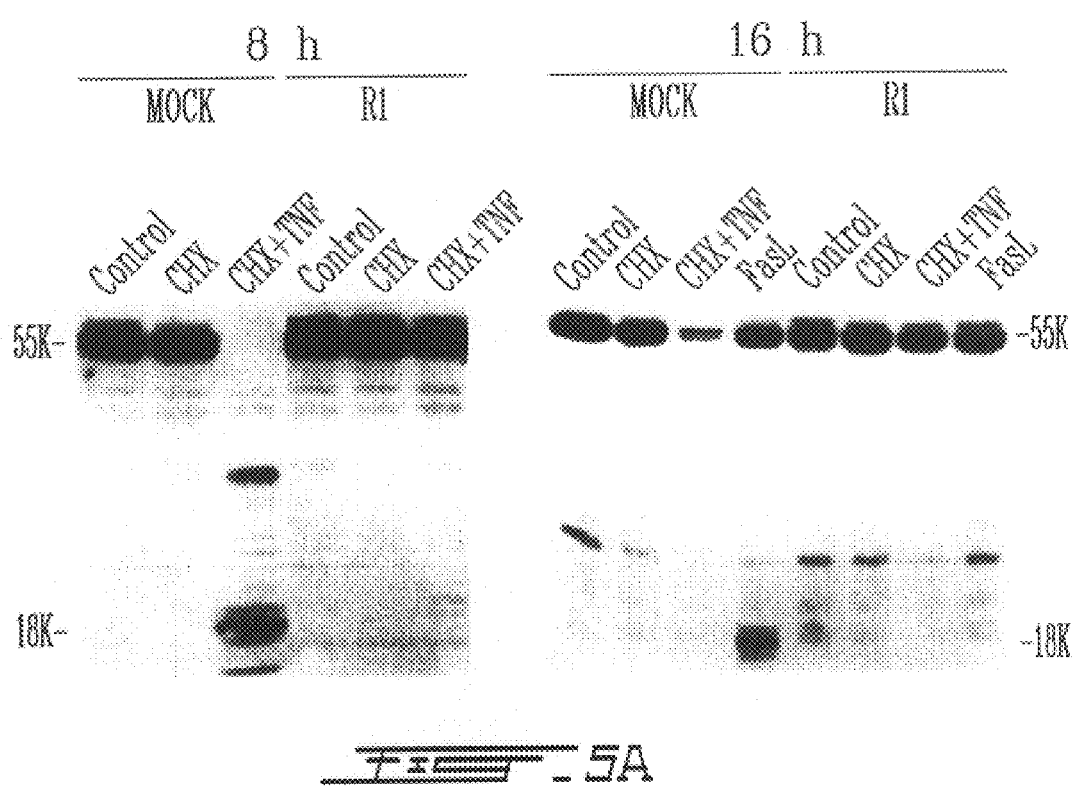

As a first step to elucidate the molecular mechanism underlying the R1 antiapoptotic activity, we evaluated the activation of caspase 8 induced either by TNF-α+CHX treatment or by Fas-L expression in A549-tTA cells with or without prior infection with Ad5TR5-R1. Caspase 8 activation was monitored by immunoblot analyses with an anti-serum visualizing the inactive 56-kDa proform and the active 18-kDa species (FIG. 5A) and by an in vitro assay using ETD-AFC as caspase 8 specific fluorescent substrate (FIG. 5B). In FIG. 5a, caspase 8 activation induced by a 8 h TNF-α+CHX treatment is clearly evidenced by the complete disappearance of the inactive 56-kDa proform and the presence of the 18k kDa active species. Time-course studies of the IETD-AFC substrate cleavage (FIG. 5B) revealed that the activation reached a maximum between 4 and 6 h post treatment and became no longer detectable at 16 h, a time where most of the cells had been destroyed by the apoptotic process. Both assays revealed that the strong activation of caspase 8 induced either by TNF-α+CHX or Fas-L expression was prevented by R1 protein expression.

The R1 segment 190–240 contains sequences exhibiting weak similarities with preferred recognition motifs for some caspases. Also, our previous observations that both the HSV-1 and -2 R1 were cleaved after one of these motifs at HSV-2 position 240. These facts led us to assess a possible inhibitory effect of the purified R1 on mature caspases 8 and 3. Our assays demonstrated that reductase-active HSV-2 R1 is unable on its own to inhibit in vitro these enzymatic activities (data not shown).

HSV inhibits TNF-α induced apoptosis. We next investigated whether during HSV infection the HSV-R1 protein could prevent apoptosis induced by TNF-α. In a first series of experiments, A549-tTA or HeLa cells were infected with either the HSV-1 strains KOS and F or the HSV-2 strain HG-52 at MOIs of 10 for 7 h before the addition of TNF- and CHX. Apoptosis was scored 20 h later by microscopic examination of the cells. The three HSV strains diminished the level of apoptosis from 95% in mock-infected control to 15–20%, levels that were similar to those obtained in HSV-infected cells treated only with CHX (see FIG. 6 for A549-tTA cells). The protective effect was confirmed by the observation that these viruses prevented the TNF-or induced PARP cleavage (see FIG. 8b for KOS strain and data not shown). In order to determine the time course of the appearance of the protective effect in HSV infected cells, A549tTA cells were infected for increasing periods before the addition of the lethal cocktail. As can be seen in FIG. 6, protection that became detectable between 2 h ½ and 4 h appeared about 1–2 h earlier with the HSV-2 strain. However, for all the three strains tested maximal protection was reached within 6 h when the levels of apoptosis became comparable to those obtained in HSV-infected cells treated only with CHX. These results suggested that the protective effect is mediated by the synthesis of immediate early or early viral protein(s).

Protection against TNF-α is reduced in cells infected by pvhs⁻, a vhs⁻ deletion mutant. As the time course of protection appearance was compatible with a down-regulating effect of the viral vhs gene, which is known to be more pronounced with HSV-2 strains, we examined the level of protection obtained with a vhs⁻ mutant. As our next obvious objective was to study ICP6Δ, the only one well characterized R1 null viral mutant that was isolated from the KOS strain of HSV-1, we chose pvhs⁻, an HSV-1 deletion mutant derived from the KOS strain (kindly provided by J. Smiley). In 3 separate experiments, the mutant exhibited a 2-fold higher level of apoptosis (35%) than the parental KOS strain (15%) (see a representative experiment in FIG. 7). This result indicated that, during the first 7 h of infection, the vhs protein contributed to the protection against TNF-α although it was not the only one involved in it.

Figure 8A:
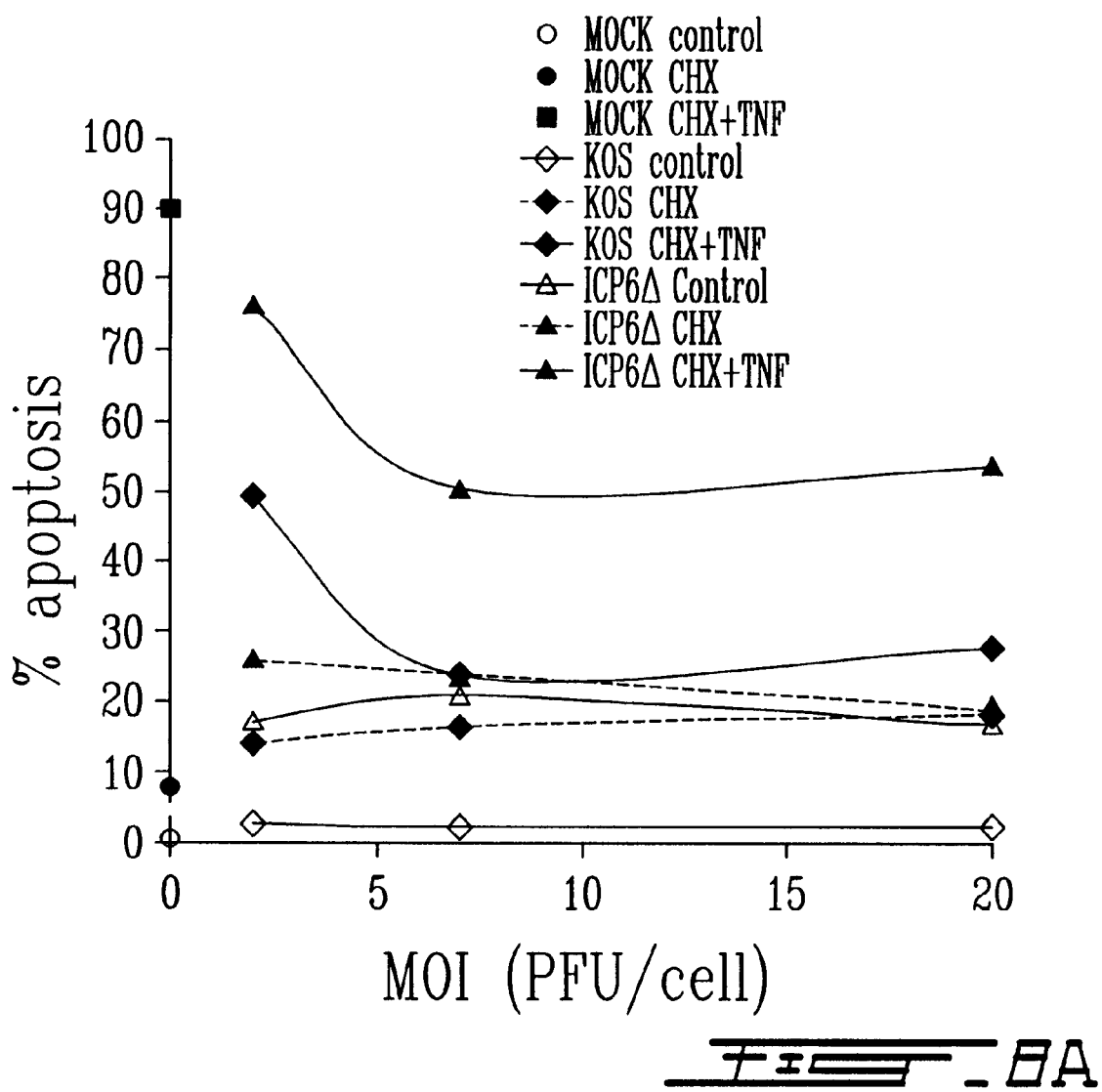
Figure 8B:
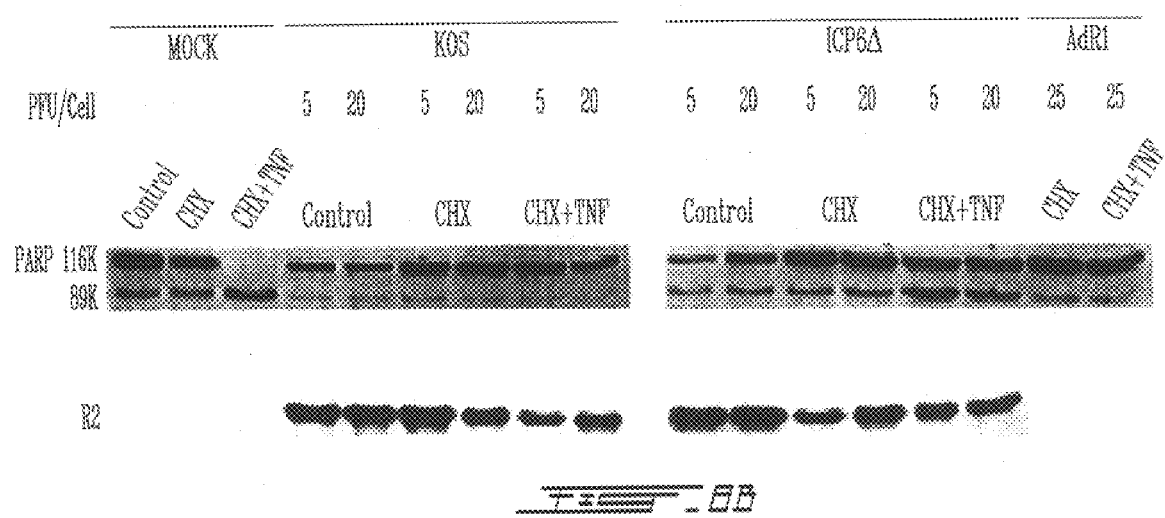

Protection against TNF-α is reduced in cells infected by ICP6Δ, an R1 deletion mutant virus. Next, we studied the effect of deleting the HSV-1 R1 gene by infecting cells with increasing MOIs of either ICP6Δ or its WT parent KOS. At the three MOIs tested, ICP6Δ showed a roughly 2-fold decreased protection (FIG. 8A). In similar experiments, the extent of apoptosis was also evaluated by examining PARP cleavage and, in addition, measuring the amount of the R2 subunit accumulated at 7 h pi was performed to monitor the level of expression of other viral proteins. These experiments as the one presented in FIG. 8B, showed that the TNF-induced PARP degradation was completely impaired in KOS-infected cells but only partially in ICP6A-infected cells. The R2 subunit accumulated at similar levels in both series of infected cells indicating that the R1 deletion did not affect the synthesis of other viral polypeptides as it had been previously reported (9). Finally, monitoring the cleavage of the caspase 8 specific substrate in A549-tTA cells infected with either WT KOS or ICP6A at 4 and 24 h p.i. demonstrated that caspase 8 activation which was completely impaired in cells infected with the WT virus significantly occurred in cells infected with the R1 null mutant, the activity being 3-fold higher than in the mock-infected control (FIG. 9).

Altogether these results demonstrate that the HSV-1 R1 plays an important role in the protection of HSV-infected cells against TNF-α. They also indicate that other viral protein (s) are involved.

Therefore compositions comprising any complementary anti-apoptotic agents are within the scope of this invention. Such complementary agents may include without being restricted thereto, agents such as anti-caspase molecules (such as enzymatic inhibitors, inhibitors of synthesis or activation, antibodies or other ligands), anti-cytokines such as anti-TNFα molecules (antagonists, degradation activators or inhibitors of synthesis or of secretion, antibodies or other ligands), a bcl-2 protein, hormologue or mimetic, anti-Fas-L molecules (antagonists, degradation activators, or inhibitors of synthesis or secretion), and agents interfering with the recruitment, binding and/or activity of cytotoxic white blood cells at a diseased tissue site.

Of course, any means by which the R1 anti apoptotic protein, variant or part may be delivered to a target tissue is within the scope of this invention. Nucleic acids encoding the anti-apoptotic molecules and recombinant nucleic acids expressing the same are such means. The nucleic acids are preferably inserted in a transfection expression vector, which is compatible with a host cell wherein prevention of apoptosis is sought. More preferably, the expression of the nucleic acids is inducible. Viral vectors are amongst those preferred for transfecting mammalian cell. These vectors can be genetically engineered to be non-infectious. They may further be inducible by adding elements responsive to an inducing agent. The inducing agent may be expressed by another vector by co-transfection (trans activation). The expression vector may also be modified to encode trageting ligand to ensure that the vector encoding RI is captured specificially by the target tissue. Finally, recombinant vectors may be compatible with hosts like bacteria, yeast and insect cells. These recombinant hosts my be used to produce the anti-apoptotic molecules of this invention. The same may be purified, if needed, by known techniques including immuno affinity chromatography with the aid of a RI ligand like a anti-RI antibody, fixed onto a solid support.

Although the present invention has been described hereinabove by way of a preferred embodiment thereof, this embodiment can be subject to modifications well know from the skilled artisan without departing from the spirit and nature of the subject invention. These modifications are within the scope of this invention as defined in the appended claims.

TABLE 1

R1 NH2 domain is sufficient for protection against TNF-α.

| Transfected pasmid | Doxycycline | |
|---|---|---|
| | with | without |
| | % apoptosis | |
| pAdTR5-K7-GFP$_Q$ | 95 | 92 |
| pAdTR5-R1-K7-GFP$_Q$ | 50 | 90 |
| pAdTR5-R1(Δ399-1 144)-K7-GFP$_Q$ | 45 | 93 |

293-TET on cells (Clontech) transiently transfected with 5 μg of plasmid DNA using the calcium phosphate technique with or without 3 ng/ml doxycycline were treated 18 h after the transfection with TNF+CHX. % apoptosis was determined 24 h later by direct microscopic observation of the cells as described in FIG. 2A.

References

1. Halford, W. P., B. M. Gebhardt, and D. J. J. Carr. 1996. Mechanisms Of Herpes Simplex Virus Type 1 Reactivation. *Journal of Virology* 70, no. 8:5051–5060.
2. Nichol, P. F., J. Y. Chang, E. M. Johnson, and P. D. Olivo. 1996. Herpes Simplex Virus Gene Expression In Neurons—Viral Dna Synthesis Is a Critical Regulatory Event In the Branch Point Between the Lytic and Latent Pathways. *Journal of Virology* 70, no. 8:5476–5486.
3. Talsinger, R., T. M. Lasner, W. Podrzucki, A. Skokotas, J. J. Leary, S. L. Berger, and N. W. Fraser. 1997. Gene Expression During Reactivation Of Herpes Simplex Virus Type 1 From Latency In the Peripheral Nervous System Is Different From That During Lytic Infection Of Tissue Cultures. *Journal of Virology* 71, no. 7:5268–5276.
4. Fawl, R. L., and B. Roizman. 1993. Induction of reactivation of herpes simplex virus in murine sensory ganglia in vivo by cadmium. *Journal of Virology* 67, no. 12:7025–31.
5. Jerome, K. R., J. F. Tait, D. M. Koelle, and L. Corey: 1998. Herpes Simplex Virus Type 1 Renders Infected Cells Resistant to Cytotoxic T-Lymphocyte-lnduced Apoptosis. *Journal of Virology* 72, no. 1 :436–441.
6. Conner, J., H. Marsden, and B. H. Clements. 1994. R1 bonucleotide reductase of herpesviruses. *Rev. Med. Virol.* 4:25–34.
7. Nikas, I., J. McLauchlan, A. J. Davison, W. R. Taylor, and J. B. Clements. 1986. Structural features of ribonucleotide reductase. *Proteins* 1, no. 4:376–84.
8. Swain, M. A., and D. A. Galloway. 1986. Herpes simplex virus specifies two subunits of ribonucleotide reductase encoded by 3'-coterminal transcripts. *Journal of Virology* 57, no. 3:802–8.
9. Goldstein, D. J., and S. K. Weller. 1988. Factor(s) present in herpes simplex virus type 1-infected cells can compensate for the loss of the large subunit of the viral ribonucleotide reductase: characterization of an ICP6 deletion mutant. *Virology* 166, no. 1:41–51.
10. Goldstein, D. J., and S. K. Weller. 1988. Herpes simplex virus type 1-induced ribonucleotide reductase activity is dispensable for virus growth and DNA synthesis: isolation and characterization of an ICP6 lacZ insertion mutant. *Journal of Virology* 62, no. 1: 196–205.
11. Idowu, A. D., E. B. Fraser-Smith, K. L. Poffenberger, and R. C. Herman. 1992. Deletion of the herpes simplex virus type 1 ribonucleotide reductase gene alters virulence and latency in vivo. *Antiviral Research* 17, no. 2: 145–56.

12. Preston, V. G., A. J. Darling, and I. M. McDougall. 1988. The herpes simplex virus type 1 temperature-sensitive mutant ts1222 has a single base pair deletion in the small subunit of ribonucleotide reductase. *Virology* 167, no. 2:458–67.

13. Jacobson, J. G., D. A. Leib, D. J. Goldstein, C. L. Bogard, P. A. Schaffer, S. K. Weller, and D. M. Coen. 1989. A herpes simplex virus ribonucleotide reductase deletion mutant is defective for productive acute and reactivatable latent infections of mice and for replication in mouse cells. *Virology* 173, no. 1: 276–83.

14. Cameron, J. M., I. McDougall, H. S. Marsden, V. G. Preston, D. M. Ryan, and J. H. Subak-Sharpe. 1988. Ribonucleotide reductase encoded by herpes simplex virus is a determinant of the pathogenicity of the virus in mice and a valid antiviral target. *Journal of General Virology* 69, no. Pt 10:2607–12.

15. Brandt, C. R., R. L. Kintner, A. M. Pumfery, R. J. Visalli, and D. R. Grau. 1991. The herpes simplex virus ribonucleotide reductase is required for ocular virulence. *Journal of General Virology* 72, no. Pt 9:2043–9.

16. Yamada, Y., H. Kimura, T. Morishima, T. Daikoku, K. Maeno, and Y. Nishiyama, 1991. The pathogenicity of ribonucleotide reductase-null mutants of herpes simplex virus type 1 in mice. *Journal of Infectious Diseases* 164, no. 6: 1091–7.

17. Paradis, H., P. Gaudreau, B. Massie, N. Lamarche, C. Guilbault, S. Gravel, and Y. Langelier. 1991. Affinity purification of active subunit 1 of herpes simplex virus type 1 ribonucleotide reductase exhibiting a protein kinase activity. *Journal of Biological Chemistry* 266, no. 15:9647–51.

18. Conner, J., J. Cooper, J. Furlong, and J. B. Clements. 1992. An autophosphorylating but not transphosphorylating activity is associated with the unique N terminus of the herpes simplex virus type 1 ribonucleotide reductase large subunit. *Journal of Virology* 66, no. 12:7511–6.

19. Cooper, J., J. Conner, and J. B. Clements. 1995. Characterization of the novel protein kinase activity present in the R1 subunit of herpes simplex virus ribonucleotide reductase. *Journal of Virology* 69, no. 8:4979–85.

20. Chung, T. D., J. P. Wymer, C. C. Smith, M. Kulka, and L. Aurelian. 1989. Protein kinase activity associated with the large subunit of herpes simplex virus type 2 ribonucleotide reductase (ICP10). *Journal of Virology* 63, no. 8:3389–98.

21. Hunter, J. C. R., C. C. Smith, and L. Aurelian. 1995. The Hsv-2 La-1 Oncoprotein Is a Member Of a Novel Family Of Serine Threonine Receptor Kinases. *International Journal of Oncology* 7, no. 3:515–522.

22. Peng, T., J. R. C. Hunter, and J. W. Nelson. 1996. The Novel Protein Kinase Of the Rr1 Subunit Of Herpes Simplex Virus Has Autophosphorylation and Transphosphorylation Activity That Differs In Its Atp Requirements For Hsv-1 and Hsv-2. *Virology* 216, no. 1: 184–196.

23. Nelson, J. W., J. Zhu, C. C. Smith, M. Kulka, and L. Aurelian. 1996. Atp and Sh3 Binding Sites In the Protein Kinase Of the Large Subunit Of Herpes Simplex Virus Type 2 Of Ribonucleotide Reductase (Icp10). *Journal of Biological Chemistry* 271, no. 29:17021–17027.

24. Smith, C. C., and L. Aurelian. 1997. The Large Subunit Of Herpes Simplex Virus Type 2 Ribonucleotide Reductase (Icp10) Is Associated With the Virion Tegument and Has Pk Activity. *Virology* 234, no. 2:235–242.

25. Langelier, Y., L. Champoux, M. Hamel, C. Guilbault, N. Lamarche, P. Gaudreau, and B. Massie. 1998. The R1 subunit of herpes simplex virus ribonucleotide reductase is a good substrate for host cell protein kinases but is not itself a protein kinase. *J Biol Chem* 273, no. 3: 1435–43.

26. Conner, J. 1999. The unique N terminus of herpes simplex virus type 1 ribonucleotide reductase large subunit is phosphorylated by casein kinase 2, which may have a homologue in *Escherichia coli*. *J Gen Virol* 80, no. Pt 6: 1471–6.

27. Massie, B., F. Couture, L. Lamoureux, D. D. Mosser, C. Guilbault, P. Jolicoeur, F. Belanger, and Y. Langelier. 1998. Inducible overexpression of a toxic protein by an adenovirus vector with a tetracycline-regulatable expression cassette. *J Virol* 72, no. 3:2289–96.

28. Graham, F. L., J. Smiley, W. C. Russell, and R. Nairn. 1977. Characteristics of a human cell line transformed by DNA from human adenovirus type 5. *J Gen Virol* 36, no. 1 :59–74.

29. Garnier, A., J. Cote, I. Nadeau, A. Kamen, and B. Massie. 1994. Scale-up of the adenovirus expression system for the production of recombinant protein in human 293S cells. *Cytotechnology* 15, no. 1–3:145–55.

30. Massie, B., J. Dionne, N. Lamarche, J. Fleurent, and Y. Langelier. 1995. Improved adenovirus vector provides herpes simplex virus ribonucleotide reductase R1 and R2 subunits very efficiently. *Biotechnology* (N Y) 13, no. 6:602–8.

31. Jani, A., H. Lochmuller, G. Acsadi, M. Simoneau, J. Huard, A. Garnier, G. Karpati, and B. Massie. 1997. Generation, validation, and large scale production of adenoviral recombinants with large size inserts such as a 6.3 kb human dystrophin cDNA. *J Virol Methods* 64, no. 2:111–24.

32. Massie, B., D. D. Mosser, M. Koutroumanis, I. Vittemony, L. Lamoureux, F. Couture, L. Paquet, C. Guilbault, J. Dionne, D. Chahla, P. Jolicoeur, and Y. Langelier. 1998. New adenovirus vectors for protein production and gene transfer. *Cytotechnology* 28:53–54.

33. Mittereder, N., K. L. March, and B. C. Trapnell. 1996. Evaluation of the concentration and bioactivity of adenovirus vectors for gene therapy. *J Virol* 70, no. 11 :7498–509.

34. Langelier, Y., and G. Buttin. 1981. Characterization of ribonucleotide reductase induction in BHK-21/C13 Syrian hamster cell line upon infection by herpes simplex virus (HSV). *Journal of General Virology* 57, no. Pt 1:21–31.

35. Jones, F. E., C. A. Smibert, and J. R. Smiley. 1995. Mutational analysis of the herpes simplex virus virion host shutoff protein: evidence that vhs functions in the absence of other viral proteins. *J Virol* 69, no. 8:4863–71.

36. Lamarche, N., G. Mafton, B. Massie, M. Fontecave, M. Atta, F. Dumas, P. Gaudreau, and Y. Langelier. 1996. Production of the R2 subunit of ribonucleotide reductase from herpes simplex virus with prokaryotic and eukaryotic expression systems: higher activity of R2 produced by eukaryotic cells related to higher iron-binding capacity. *Biochem J* 320, no. Pt 1 :129–35.

37. Cohen, E. A., P. Gaudreau, P. Brazeau, and Y. Langelier. 1986. Neutralization of herpes simplex virus ribonucleotide reductase activity by an oligopeptide-induced antiserum directed against subunit H2. *Journal of Virology* 90, no. 3:1130–3.

What is claimed is:

1. A method for preventing apoptosis in vitro, induced in a cell by an apoptotic component other than Herpes simplex virus ribonucleotide reductase without the N-terminal 357 amino acids thereof, which comprises the step of submitting said cell to an anti-apoptotic treatment with an anti-apoptotic agent comprising R1 subunit of Herpes simplex virus ribonucleotide reductase enzyme or a nucleic acid encoding said enzyme.

2. A method as defined in claim 1, which further comprises the step of co-administering another anti-apoptotic agent.

3. A method as defined in claim 1, wherein said anti-apoptotic treatment comprises achieving in said cell a concentration of about 0.005% R1 subunit of Herpes simplex virus ribonucleotide reductase enzyme with regard to the amount of total cellular proteins.

4. A method as defined in claim 1, wherein said apoptotic component involves TNF-$\alpha$, Fas or Caspase 8 activation in said cell.

* * * * *